United States Patent
Hwang et al.

(10) Patent No.: US 11,826,454 B2
(45) Date of Patent: Nov. 28, 2023

(54) COSMETICS COMPOSITION CONTAINING ANTI-OXIDANT

(71) Applicant: AMOREPACIFIC CORPORATION, Seoul (KR)

(72) Inventors: Yoonkyun Hwang, Yongin-si (KR); Jihye An, Yongin-si (KR); Youngsun Kim, Yongin-si (KR); Dalsu Na, Yongin-si (KR); Byungfhy Suh, Yongin-si (KR); Seonga Cho, Yongin-si (KR); Byungguen Chae, Yongin-si (KR); Dongwon Choi, Yongin-si (KR); Sanghoon Han, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 176 days.

(21) Appl. No.: 16/770,382

(22) PCT Filed: Jan. 9, 2020

(86) PCT No.: PCT/KR2020/000420
§ 371 (c)(1),
(2) Date: Jun. 5, 2020

(87) PCT Pub. No.: WO2020/091583
PCT Pub. Date: May 7, 2020

(65) Prior Publication Data
US 2020/0383895 A1    Dec. 10, 2020

(30) Foreign Application Priority Data
Feb. 14, 2019   (KR) .................. 10-2019-0017316

(51) Int. Cl.
| | |
|---|---|
| *A61K 8/67* | (2006.01) |
| *A61K 8/31* | (2006.01) |
| *A61K 8/73* | (2006.01) |
| *A61K 8/92* | (2006.01) |
| *A61Q 19/00* | (2006.01) |

(52) U.S. Cl.
CPC .............. *A61K 8/676* (2013.01); *A61K 8/31* (2013.01); *A61K 8/678* (2013.01); *A61K 8/73* (2013.01); *A61K 8/735* (2013.01); *A61K 8/922* (2013.01); *A61Q 19/00* (2013.01); *A61K 2800/48* (2013.01); *A61K 2800/522* (2013.01)

(58) Field of Classification Search
None
See application file for complete search history.

(56) References Cited

FOREIGN PATENT DOCUMENTS

| | | | | |
|---|---|---|---|---|
| CN | 107198675 A | | 9/2017 | |
| GB | 2259015 A | * | 3/1993 | ............ A61K 8/03 |
| KR | 10-2009-0089372 A | | 8/2009 | |
| KR | 10-2010-0121995 A | | 11/2010 | |
| KR | 10-2013-0060663 A | | 6/2013 | |
| KR | 10-2017-0123698 A | | 11/2017 | |
| KR | 10-1833040 B1 | | 2/2018 | |
| KR | 10-2018-0116601 A | | 10/2018 | |
| KR | 20180112053 A | * | 10/2018 | |
| KR | 10-2008275 B1 | | 8/2019 | |
| WO | 2008/076416 A1 | | 6/2008 | |
| WO | 2016/168132 A1 | | 10/2016 | |

OTHER PUBLICATIONS

Lin et al., "UV protection by combination topical antioxidants vitamin C and vitamin E", J Am Acad Dermatol Jun. 2003, vol. 48, No. 6, p. 866-874. (Year: 2003).*
International Search Report for PCT/KR2020/000420 dated Apr. 21, 2020 (PCT/ISA/210).
Communication by Chinese Patent Office dated Sep. 12, 2023, issued in Chinese Application No. 202080000481.X.

* cited by examiner

*Primary Examiner* — Gina C Justice
(74) *Attorney, Agent, or Firm* — Sughrue Mion, PLLC

(57) ABSTRACT

The present invention relates to a cosmetics composition having high anti-oxidant content. Specifically, the anti-oxidant of the present invention may be pure vitamin-C. More specifically, the present invention can maintain the potency of vitamin-C by preventing exposure of same to the outside air.

5 Claims, 13 Drawing Sheets

US 11,826,454 B2

COSMETICS COMPOSITION CONTAINING ANTI-OXIDANT

REFERENCE TO THE RELEVANT APPLICATION

This application is a National Stage of International Application No. PCT/KR2020/000420 filed Jan. 9, 2020, claiming priority based on Korean Patent Application No. 10-2019-0017316 filed on Feb. 14, 2019, and the entire contents of this application are incorporated as a reference into the present application.

TECHNICAL FIELD

This disclosure relates to a cosmetic composition having an excellent antioxidant effect of an antioxidant.

BACKGROUND ART

Vitamin C, which is a representative antioxidant used for cosmetics, has an excellent antioxidant effect but has a problem that vitamin C is chemically unstable so it is deteriorated due to sunlight, oxygen, heat, pH change, etc., and thus the titers thereof are lowered. For this reason, studies on various methods for improving oxidative stability while maintaining the efficacy of vitamin C have been conducted. These studies comprise an attempt to develop derivatives of vitamin C in order to overcome the stability, but these derivatives are not competitive in price compared to vitamin C. Accordingly, it is necessary to develop cosmetic compositions that are not easily exposed to oxygen while using vitamin C itself.

SUMMARY OF INVENTION

Technical Problem

The present disclosure provides a cosmetic composition capable of inhibiting oxidation of an antioxidant.

Solution to Problem

In order to solve the problems of the prior art technologies, the present disclosure provides, as one embodiment, a cosmetic composition comprising a double layer, comprising a layer comprising an antioxidant, and an oil layer covering the surface of said layer, wherein said oil layer comprises one or more oils selected from the group consisting of dimethicone, methyltrimethicone, hydrogenated $C_{6-14}$ olefin polymers, diphenylsiloxy phenyl trimethicone, $C_{18-21}$ alkane, and natural oils.

In addition, the present disclosure provides, as one embodiment, a cosmetic composition, comprising a double layer consisting of a first oil layer and a second oil layer, wherein said first oil layer comprises one or more oils selected from the group consisting of dimethicone, methyltrimethicone, hydrogenated $C_{6-14}$ olefin polymers, diphenylsiloxy phenyl trimethicone, $C_{18-21}$ alkane, and natural oils, and wherein said second oil layer is an oil layer covering the surface of the first oil layer and comprises hydrogenated $C_{6-14}$ olefin polymers or vegetable oils.

Advantageous Effects of Invention

The cosmetic composition according to one embodiment of the present disclosure comprises oils with an excellent oxygen blocking ability or consists an oil layer consisting of two layers, and thus, has an excellent oxygen blocking ability. In addition, in the cosmetic composition according to one embodiment of the present disclosure, the time for separating the double layer is short, so the oxygen exposure time of the antioxidant can be reduced thanks to the fast separation of the double layer, when considering the actual use environment where the composition is used by shaking.

DESCRIPTION OF EMBODIMENTS

Figure 1:
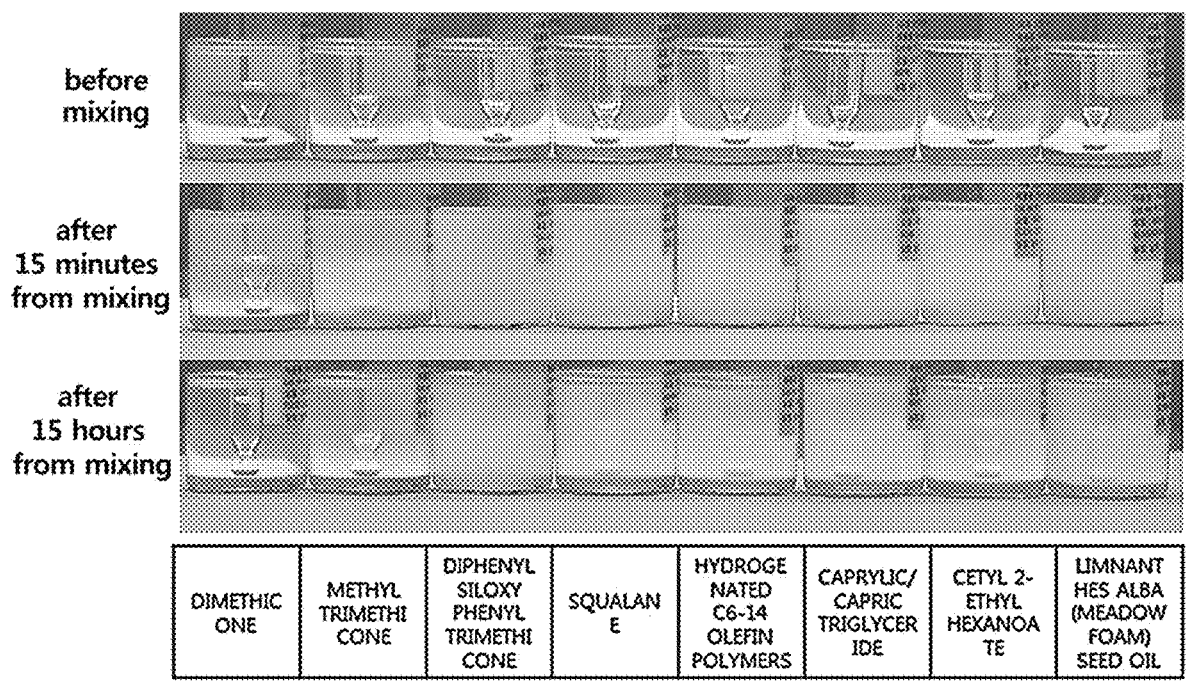
FIG. 1 is the photograph showing the comparison test results of the separation rates depending on the types of oils according to one test example of the present disclosure.

One embodiment of the present disclosure may provide a cosmetic composition comprising a double layer, comprising a layer comprising an antioxidant, and an oil layer covering the surface of said layer, wherein said oil layer comprises one or more oils selected from the group consisting of dimethicone, methyltrimethicone, hydrogenated $C_{6-14}$ olefin polymers, diphenylsiloxy phenyl trimethicone, $C_{18-21}$ alkane, and natural oils.

One embodiment of the present disclosure may provide a cosmetic composition comprising a double layer comprising: an aqueous layer containing an antioxidant; and an oil layer covering the surface of said aqueous layer.

In one embodiment, said oils are not limited as long as the oils are used for cosmetics, and the examples thereof may comprise one or more oils selected from the group consisting of dimethicone, methyltrimethicone, hydrogenated $C_{6-14}$ olefin polymers, diphenylsiloxy phenyl trimethicone, $C_{18-21}$ alkane, and natural oils. In one embodiment, the natural oil is not limited as long as the natural oil is used for cosmetics, and the examples thereof may comprise one or more selected from the group consisting of Camellia Japonica seed oil, Helianthus Annuus (Sunflower) seed oil, Meadowfoam seed oil, olive oil, grapeseed oil and Limnanthes alba seed oil. In one embodiment, said Camellia Japonica seed oil may comprise camellia seed oil. In one embodiment, said Camellia Japonica seed oil may comprise fermented Camellia Japonica seed oil. As the present invention comprises said oils in one embodiment, the layer separation occurs for a short time when the formulation comprising a double layer of said oils and an antioxidant is used by shaking. Thereby, the present invention can minimize the time when the antioxidant is in contact with oxygen, so that the antioxidant effect of an antioxidant is excellent. In addition, conventional formulations that do not comprise an oil layer have a problem that the antioxidant is easily deteriorated and the degree of modification of the formulation is severe. However, since the present invention has an excellent antioxidant effect of an antioxidant, the present invention can also effectively prevent the formulation from being discolored during use.

In one embodiment, the antioxidant may comprise vitamin C.

In one embodiment, the layer comprising the antioxidant may further comprise a thickener. In the present specification, the term "thickener" is used in its broadest sense to comprise not only the purpose of increasing the viscosity of the composition, but also the ingredients used to improve the physical stability of the composition and the feeling of use in use.

In one embodiment, said thickener is not limited as long as the thickener is used for cosmetics and does not affect the separation rate of the oil layer and the layer comprising the antioxidant, and the examples thereof may comprise one or more selected from the group consisting of hyaluronate, xanthan gum, β-glucan and biosaccharide gum-1.

In one embodiment, the composition may further comprise squalane and a fat-soluble antioxidant, and for example, said squalane and fat-soluble antioxidant may be comprised in the oil layer.

In one embodiment, said fat-soluble antioxidant is not limited as long as the fat-soluble antioxidant is used for cosmetic compositions, and the examples thereof may comprise one or more selected from the group consisting of tocopherol, lycopene and retinol.

In one embodiment, said cosmetic composition may not comprise a surfactant.

In one embodiment, said oil layer may be comprised as a double layer consisting of a first oil layer and a second oil layer. In one embodiment, said first oil layer is not limited as long as the oils are used for cosmetics, and the examples thereof may comprise one or more oils selected from the group consisting of dimethicone, methyltrimethicone, hydrogenated $C_{6-14}$ olefin polymers, diphenylsiloxy phenyl trimethicone, $C_{18-21}$ alkane, and natural oils. In one embodiment, said second oil layer may comprise hydrogenated $C_{6-14}$ olefin polymers or vegetable oils. In one embodiment, said first oil layer may be an oil layer covering the surface of the layer comprising the antioxidant, and said second oil layer may be an oil layer covering the first oil layer.

In one embodiment, the vegetable oils of said second oil layer are not limited as long as the vegetable oils are used for cosmetics, and the examples thereof may comprise one or more selected from the group consisting of Meadowfoam seed oil, Helianthus Annuus (Sunflower) seed oil, Camellia Japonica seed oil, olive oil, grapeseed oil and Limnanthes alba seed oil. In one embodiment, said Camellia Japonica seed oil may comprise camellia seed oil. In one embodiment, said Camellia Japonica seed oil may comprise fermented Camellia Japonica seed oil.

In one embodiment, said second oil layer may further comprise tocopherol and a fat-soluble antioxidant.

In one embodiment, said fat-soluble antioxidant is not limited as long as the fat-soluble antioxidant is used for cosmetics, and the examples thereof may comprise tocopherol, lycopene or a combination thereof.

In one embodiment, the amount of the antioxidant may be 15 to 35 wt. % with respect to the total weight of the composition. Specifically, the amount of the vitamin C may be 15 wt. % or more, 18 wt. % or more, 20 wt. % or more, 21 wt. % or more, 22 wt. % or more, 23 wt. % or more, 24 wt. % or more or 25 wt. % or more, and 35 wt. % or less, 32 wt. % or less, 30 wt. % or less, 29 wt. % or less, 28 wt. % or less, 27 wt. % or less or 26 wt. % or less, with respect to the total weight of the composition.

In one embodiment, the amount of the oil layer may be 3 to 50 wt. % with respect to the total weight of the composition. Specifically, the amount of the oil layer may be 3 wt. % or more, 8 wt. % or more, 13 wt. % or more, 18 wt. % or more, 19 wt. % or more, 20 wt. % or more, 21 wt. % or more, 22 wt. % or more, 23 wt. % or more, 24 wt. % or more or 25 wt. % or more, and 50 wt. % or less, 45 wt. % or less, 40 wt. % or less, 35 wt. % or less, 30 wt. % or less, 29 wt. % or less, 28 wt. % or less, 27 wt. % or less, or 26 wt. % or less with respect to the total weight of the composition. More specifically, the amount of the oil layer may be 3 wt. % or more, 4 wt. % or more, 5 wt. % or more, 6 wt. % or more or 7 wt. % or more, and 12 wt. % or less, 11 wt. % or less, 10 wt. % or less, 9 wt. % or less, or 8 wt. % or less, with respect to the total weight of the composition.

In one embodiment, the weight ratio of the first oil layer to the second oil layer may be 30:1 to 1:30. Specifically, the weight ratio may be 27:1 or more, 24:1 or more, 21:1 or more, 18:1 or more, 15:1 or more, 12:1 or more, 9:1 or more, 8:1 or more, 7:1 or more, 6:1 or more, 5:1 or more, 4.5:1 or more, 4:1 or more, 3.5:1 or more, 3:1 or more, 2.5:1 or more, 2:1 or more or 1.5:1 or more, and 1:30 or less, 1:27 or less, 1:24 or less, 1:21 or less, 1:18 or less, 1:15 or less, 1:12 or less, 1:9 or less, 1:8 or less, 1:7 or less, 1:6 or less, 1:5 or less, 1:4.5 or less, 1:4 or less, 1:3.5 or less, 1:3 or less, 1:2.5 or less, or 1:2 or less. More specifically, the weight ratio of the first oil layer to the second oil layer may be 2:1 or more, 1.9:1 or more, 1.8:1 or more, 1.5:1 or more, 1.4:1 or more, 1.3:1 or more, 1.2:1 or more or 1.1:1 or more, and 1:1.9 or less, 1:1.8 or less, 1:1.7 or less, 1:1.6 or less, 1:1.5 or less, 1:1.4 or less, 1:1.3 or less, or 1:1.2 or less.

Embodiments

Hereinafter, the present invention will be explained in more detailed with reference to the examples. It is obvious to a person having ordinary knowledge in the art that these examples are presented just to exemplify the present invention, and it is not interpreted that the scope of the present invention is limited by these examples.

Comparison Test of the Separation Rates Depending on the Types of Oils

The test was conducted to compare the time of separating the double layer by shaking the two-layer cosmetic composition in which an oil layer is present on the layer comprising vitamin C as an antioxidant. The composition used for the test is shown in Table 1.

As a test result, it was found that there was a difference in the time of separating the layers depending on the type of oils. The photographs showing the separation before mixing, after 15 minutes from mixing and after 15 hours from mixing are shown in FIG. 1. Referring to the results after 15 minutes from mixing and after 15 hours from mixing, in the other oils of the comparative examples except for dimethicone and methyltrimethicone, almost no layer separation was observed. Accordingly, in the case of shaking and using a product in which an oil layer is separated from a layer comprising an antioxidant, the use of dimethicone or methyltrimethicone in the oil layer leads to a layer separation in a short time, which results in reducing the time of vitamin

TABLE 1

| INCI | Example 1 | Example 2 | Example 3 | Comparative Example 1 | Example 4 | Comparative Example 2 | Comparative Example 3 | Example 5 |
|---|---|---|---|---|---|---|---|---|
| Water | | | | To 100 | | | | |
| Disodium EDTA | 0.05 | 0.05 | 0.05 | 0.05 | 0.05 | 0.05 | 0.05 | 0.05 |
| Propanediol | 10 | 10 | 10 | 10 | 10 | 10 | 10 | 10 |
| Ascorbic acid | 25 | 25 | 25 | 25 | 25 | 25 | 25 | 25 |
| Acid yellow 23 | 0.0007 | 0.0007 | 0.0007 | 0.0007 | 0.0007 | 0.0007 | 0.0007 | 0.0007 |
| Glutathione | 0.1 | 0.1 | 0.1 | 0.1 | 0.1 | 0.1 | 0.1 | 0.1 |
| Sodium hyaluronate | — | — | — | — | — | — | — | — |
| Xanthan gum | 0.4 | 0.4 | 0.4 | 0.4 | 0.4 | 0.4 | 0.4 | 0.4 |
| Beta-glucan | — | — | — | — | — | — | — | — |
| Biosaccharide gum-1 | — | — | — | — | — | — | — | — |
| Dimethicone | 5 | — | — | — | — | — | — | — |
| Hydrogenated $C_{6-14}$ olefin polymers | — | — | — | — | 5 | — | — | — |
| Methyl trimethicone | — | 5 | — | — | — | — | — | — |
| Diphenylsiloxy phenyl trimethicone | — | — | 5 | — | — | — | — | — |
| $C_{18-21}$ alkane | — | — | — | — | — | — | — | — |
| Meadowfoam seed oil | — | — | — | — | — | — | — | 5 |
| *Helianthus Annuus* (sunflower) seed oil | — | — | — | — | — | — | — | — |
| Squalane | — | — | — | 5 | — | — | — | — |
| Tocopherol | — | — | — | — | — | — | — | — |
| *Solanum lycopersicum* (tomato) fruit lipids | — | — | — | — | — | — | — | — |
| Caprylic/capric triglyceride | — | — | — | — | — | 5 | — | — |
| Cetyl 2-ethyl hexanoate | — | — | — | — | — | — | 5 | — |
| Polysorbate 20 | — | — | — | — | — | — | — | — |
| PEG-60 hydrogenated castor oil | — | — | — | — | — | — | — | — |
| Fragrance | 0.15 | 0.15 | 0.15 | 0.15 | 0.15 | 0.15 | 0.15 | 0.15 |

In Examples 1 to 5 and Comparative Examples 1 to 3, other ingredients were used in the same amount, with only types of oils being different. In Example 1, dimethicone was used; in Example 2, methyltrimethicone was used; in Example 3, diphenylsiloxy phenyl trimethicone was used; in Comparative Example 1, squalane was used; in Example 4, hydrogenated $C_{6-14}$ olefin polymers were used; in Comparative Example 2, caprylic/capric triglyceride was used; in Comparative Example 3, cetyl 2-ethyl hexanoate was used; and in Example 5, Meadowfoam seed oil was used.

C, which is the antioxidant, being in contact with oxygen, and thereby, its antioxidant effect is excellent.

Test for Separation Rates Depending on the Presence of a Surfactant

Figure 2:
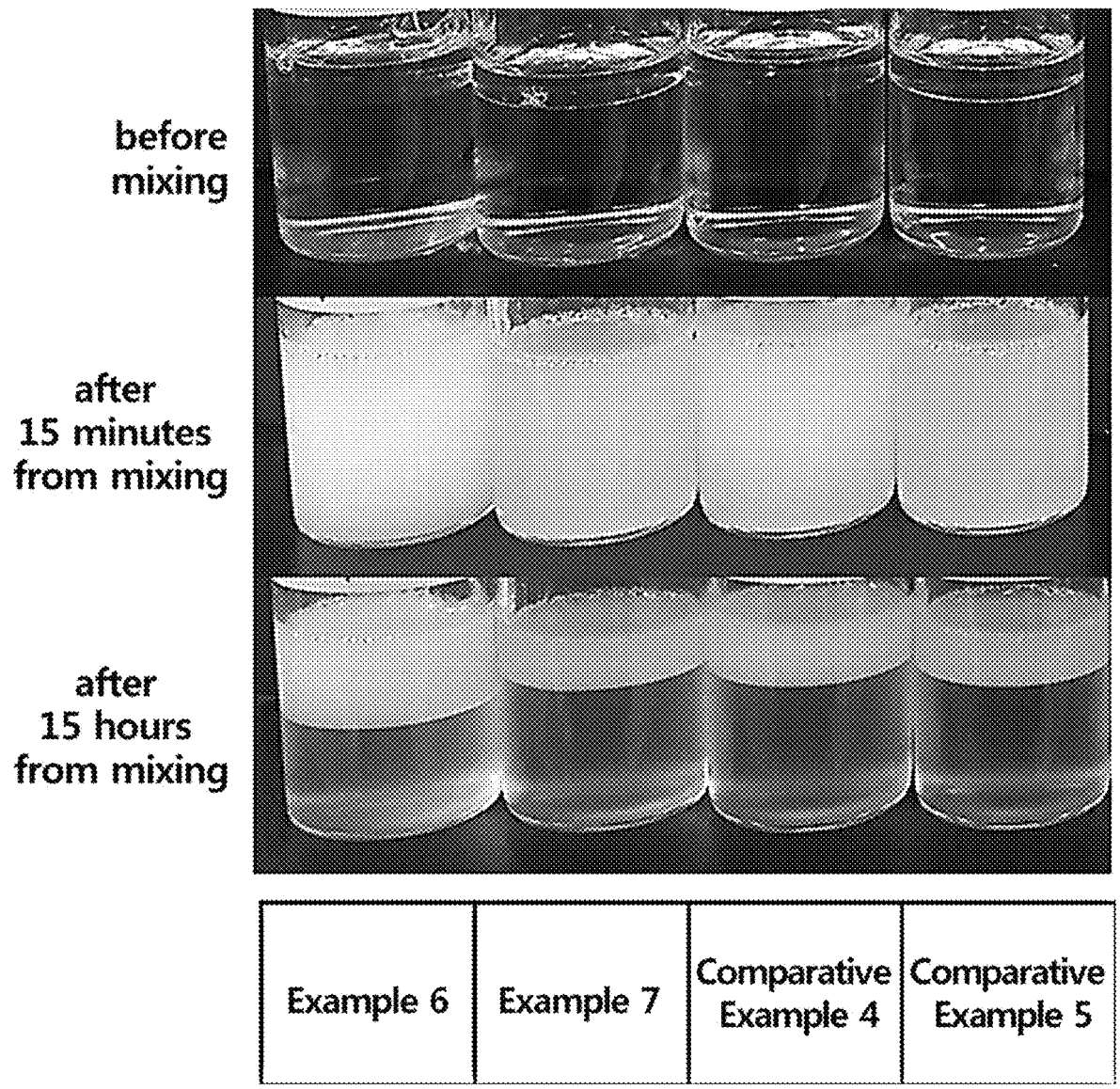
FIG. 2 is the photograph showing the test results of comparing separation rate of the compositions comprising a surfactant, according to one test example of the present disclosure.

The test was conducted for the effect of the surfactant on the separation rates in the case where a surfactant is present in the oil layer. This test was performed with the composition of Table 2, and the results are shown in FIG. 2.

TABLE 2

| INCI | Example 6 | Example 7 | Comparative Example 4 | Comparative Example 5 |
|---|---|---|---|---|
| Water | To 100 | To 100 | To 100 | To 100 |
| Disodium EDTA | 0.05 | 0.05 | 0.05 | 0.05 |
| Propanediol | 10 | 10 | 10 | 10 |
| Ascorbic acid | 25 | 25 | 25 | 25 |
| Acid yellow 23 | 0.0007 | 0.0007 | 0.0007 | 0.0007 |
| Glutathione | 0.1 | 0.1 | 0.1 | 0.1 |
| Sodium hyaluronate | 0.4 | 0.4 | 0.4 | 0.4 |
| Xanthan gum | — | — | — | — |
| Beta-glucan | — | — | — | — |
| Biosaccharide gum-1 | — | — | — | — |
| Dimethicone | 5 | 5 | — | — |
| Hydrogenated $C_{6-14}$ olefin polymers | — | — | — | — |
| Methyl trimethicone | — | — | — | — |
| Diphenylsiloxy phenyl trimethicone | — | — | — | — |
| $C_{18-21}$ alkane | — | — | — | — |
| Meadowfoam seed oil | — | — | — | — |
| *Helianthus Annuus* (sunflower) seed oil | — | — | — | — |
| Squalane | — | — | — | — |
| Tocopherol | 0.5 | 0.5 | — | — |
| *Solanum lycopersicum* (tomato) fruit lipids | 0.0005 | 0.0005 | — | — |
| Caprylic/capric triglyceride | — | — | 5 | 5 |
| Cetyl 2-ethyl hexanoate | — | — | — | — |
| Polysorbate 20 | 0.5 | — | 0.5 | — |
| PEG-60 hydrogenated castor oil | — | 0.5 | — | 0.5 |
| Fragrance | 0.15 | 0.15 | 0.15 | 0.15 |

In Example 6 and Comparative Example 4, polysorbate 20 was used as a surfactant; and in Example 7 and Comparative Example 5, PEG-60 hydrogenated castor oil was used as a surfactant. It can be observed that in the case where the surfactant was comprised in an oil layer, when the oil layer and the layer comprising the antioxidant are mixed by shaking, the separation rate became slow due to the surfactant in the oil layer, and the surfactant forms an opaque layer in which water and oil are mixed. From this, it can be considered that since the separation rate is slow, the time of vitamin C being exposed to air gets longer, and the appearance is not good because of the opaque layer formed after the separation. Also, due to the surfactant, the oil is mixed in the layer comprising the antioxidant, so the thickness of the oil layer is reduced, which may adversely affect the oxidation inhibiting ability.

Comparison Test of the Separation Rates According to the Use of a Thickener (1) Comparative Test With Different Thickeners As the layer separation takes longer time, the time of vitamin C being exposed to air would be longer to oxidize vitamin C. Since a thickener should be comprised in the cosmetic to enhance the feeling of use, there is a need to select and use a thickener with a fast layer separation rate. Thus, using the composition of Table 3 in which dimethicone was used as an oil phase with different thickeners, the comparison test of the separation rates depending on the use of thickeners was conducted.

TABLE 3

| INCI | Example 8 | Example 9 | Example 10 | Example 11 | Example 12 |
|---|---|---|---|---|---|
| Water | To 100 | To 100 | To 100 | To 100 | To 100 |
| Disodium EDTA | 0.05 | 0.05 | 0.05 | 0.05 | 0.05 |
| Propanediol | 10 | 10 | 10 | 10 | 10 |
| Ascorbic acid | 25 | 25 | 25 | 25 | 25 |
| Acid yellow 23 | 0.0007 | 0.0007 | 0.0007 | 0.0007 | 0.0007 |
| Glutathione | 0.1 | 0.1 | 0.1 | 0.1 | 0.1 |
| Sodium hyaluronate | — | 0.4 | — | — | — |
| Xanthan gum | — | — | 0.4 | — | — |
| Beta-glucan | — | — | — | 3 | — |
| Biosaccharide gum-1 | — | — | — | — | 3 |
| Dimethicone | 5 | 5 | 5 | 5 | 5 |
| Hydrogenated $C_{6-14}$ olefin polymers | — | — | — | — | — |
| Methyl trimethicone | — | — | — | — | — |
| Diphenylsiloxy phenyl trimethicone | — | — | — | — | — |

TABLE 3-continued

| INCI | Example 8 | Example 9 | Example 10 | Example 11 | Example 12 |
|---|---|---|---|---|---|
| $C_{18-21}$ alkane | — | — | — | — | — |
| Meadowfoam seed oil | — | — | — | — | — |
| *Helianthus Annuus* (sunflower) seed oil | — | — | — | — | — |
| Squalane | — | — | — | — | — |
| Tocopherol | 0.5 | 0.5 | 0.5 | 0.5 | 0.5 |
| *Solanum lycopersicum* (tomato) fruit lipids | 0.0005 | 0.0005 | 0.0005 | 0.0005 | 0.0005 |
| Caprylic/capric triglyceride | — | — | — | — | — |
| Cetyl 2-ethyl hexanoate | — | — | — | — | — |
| Polysorbate 20 | — | — | — | — | — |
| PEG-60 hydrogenated castor oil | — | — | — | — | — |
| Fragrance | 0.15 | 0.15 | 0.15 | 0.15 | 0.15 |

In Example 8, a thickener was not used; in Example 9, sodium hyaluronate was used; in Example 10, xanthan gum was used; in Example 11, beta glucan was used; and in Example 12, biosaccharide Gum-1 was used.

As a result of comparing the separation rates, the separation rate was lowered in the order of Example 8, Example 9, Example 11, Example 12, and Example 10. The phases were separated within 1 minute in Example 8, within 2 minutes in Example 9, within 2 minutes 30 seconds in Example 11, within 3 minutes in Example 12, and more than 10 minutes in Example 10. From this, it was confirmed that the case comprising sodium hyaluronate used in Example 9 was excellent in the separation rate.

(2) Test Comprising Different Oils with the Same Thickener

Figure 3:
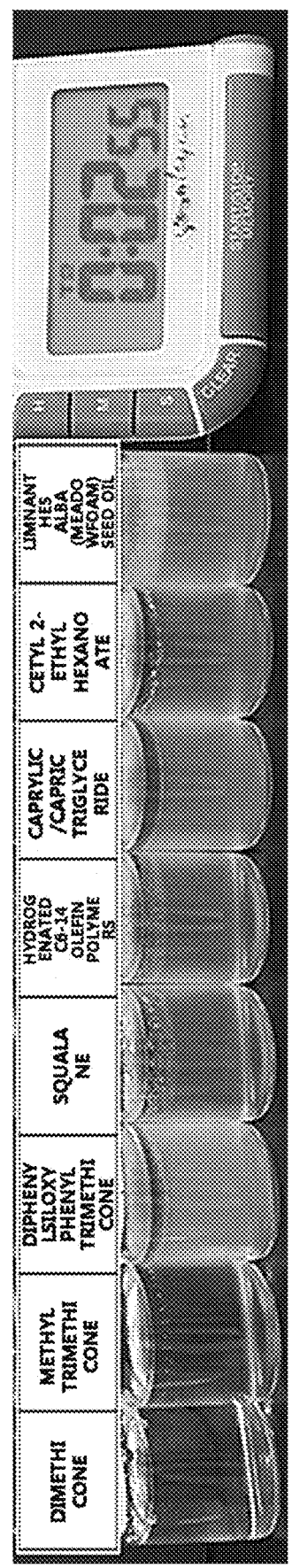
FIG. 3 is the photograph showing the comparison test results of the separation rates of the compositions in which sodium hyaluronate was used as a thickener, with only types of oils comprised in the oil layer being different, according to one test example of the present disclosure.

Comparison test of the separation rates of the compositions, comprising sodium hyaluronate which does not affect the separation rate as confirmed in said test example, with oils being different, was conducted. The test was conducted with the composition of Table 4, and the result is shown in FIG. 3.

TABLE 4

| INCI | Example 13 | Example 14 | Example 15 | Comparative example 6 | Example 16 | Comparative example 7 | Comparative example 8 | Example 17 | Example 18 | Example 19 |
|---|---|---|---|---|---|---|---|---|---|---|
| Water | To 100 | To 100 | To 100 | To 100 | To 100 | To 100 | To 100 | To 100 | To 100 | To 100 |
| Disodium EDTA | 0.05 | 0.05 | 0.05 | 0.05 | 0.05 | 0.05 | 0.05 | 0.05 | 0.05 | 0.05 |
| Propanediol | 10 | 10 | 10 | 10 | 10 | 10 | 10 | 10 | 10 | 10 |
| Ascorbic acid | 25 | 25 | 25 | 25 | 25 | 25 | 25 | 25 | 25 | 25 |
| Acid yellow 23 | 0.0007 | 0.0007 | 0.0007 | 0.0007 | 0.0007 | 0.0007 | 0.0007 | 0.0007 | 0.0007 | 0.0007 |
| Glutathione | 0.1 | 0.1 | 0.1 | 0.1 | 0.1 | 0.1 | 0.1 | 0.1 | 0.1 | 0.1 |
| Sodium hyaluronate | 0.4 | 0.4 | 0.4 | 0.4 | 0.4 | 0.4 | 0.4 | 0.4 | 0.4 | 0.4 |
| Xanthan gum | — | — | — | — | — | — | — | — | — | — |
| Beta-glucan | — | — | — | — | — | — | — | — | — | — |
| Biosaccharide gum-1 | — | — | — | — | — | — | — | — | — | — |
| Dimethicone | 5 | — | — | — | — | — | — | — | — | — |
| Hydrogenated $C_{6-14}$ olefin polymers | — | — | — | — | 5 | — | — | — | — | — |
| Methyl trimethicone | — | 5 | — | — | — | — | — | — | — | — |
| Diphenylsiloxy phenyl trimethicone | — | — | 5 | — | — | — | — | — | — | — |
| $C_{18-21}$ alkane | — | — | — | — | — | — | — | — | 5 | — |
| Meadowfoam seed oil | — | — | — | — | — | — | — | 5 | — | — |
| *Helianthus Annuus* (sunflower) seed oil | — | — | — | — | — | — | — | — | — | 5 |
| Squalane | — | — | — | 5 | — | — | — | — | — | — |
| Tocopherol | 0.5 | 0.5 | 0.5 | 0.5 | 0.5 | 0.5 | 0.5 | 0.5 | 0.5 | 0.5 |
| *Solanum lycopersicum* (tomato) fruit lipids | 0.0005 | 0.0005 | 0.0005 | 0.0005 | 0.0005 | — | — | 0.0005 | 0.0005 | 0.0005 |

TABLE 4-continued

| INCI | Example 13 | Example 14 | Example 15 | Comparative example 6 | Example 16 | Comparative example 7 | Comparative example 8 | Example 17 | Example 18 | Example 19 |
|---|---|---|---|---|---|---|---|---|---|---|
| Caprylic/capric triglyceride | — | — | — | — | — | 5 | — | — | — | — |
| Cetyl 2-ethyl hexanoate | — | — | — | — | — | — | 5 | — | — | — |
| Polysorbate 20 | — | — | — | — | — | — | — | — | — | — |
| PEG-60 hydrogenated castor oil | — | — | — | — | — | — | — | — | — | — |
| Fragrance | 0.15 | 0.15 | 0.15 | 0.15 | 0.15 | 0.15 | 0.15 | 0.15 | 0.15 | 0.15 |

Examples 13 to 19 and Comparative Examples 6 to 8 all comprised sodium hyaluronate as a thickener. Dimethicone in Example 13, methyltrimethicone in Example 14, diphenylsiloxy phenyl trimethicone in Example 15, squalane in Comparative Example 6, hydrogenated $C_{6-14}$ olefin polymers in Example 16, caprylic/capric triglyceride in Comparative Example 7, cetyl 2-ethyl hexanoate in Comparative Example 8, meadowfoam seed oil in Example 17, $C_{18-21}$ alkane in Example 18, and sunflower seed oil in Example 19 were used in the oil layer, respectively.

As the result, in all examples, the phase separation occurred within 3 minutes after shaking and mixing. In particular, in the case of Examples 13 to 15, 18 and 19 using silicone-based oils, it was observed that the layer separation occurred 30 seconds after shaking, thereby minimizing the air exposure time of the layer comprising the antioxidant.

Comparative Test of the Separation Rate of the Composition, in which the Oil Layer Consists of Double Layer In Examples 18 to 20 and Comparative Examples 9 to 11, the oil layer consisted of a double layer. That is, the composition was prepared such that the first oil layer covered the surface of the layer comprising the antioxidant with vitamin C, and the second oil layer covered the surface of the first oil layer. As the first oil layers in Examples 18 to 20 and Comparative Examples 9 to 11, dimethicone was used; and as the second oil layer, a hydrogenated $C_{6-14}$ olefin polymer was used in Example 18, Meadowfoam seed oil in Example 19, sunflower seed oil in Example 20, methyltrimethicone in Comparative Example 9, diphenylsiloxy phenyl trimethicone in Comparative Example 10, and $C_{18-21}$ alkane in Comparative Example 11. The entire composition is shown in Table 5 below.

TABLE 5

| INCI | Example 20 | Example 21 | Example 22 | Comparative example 9 | Comparative example 10 | Comparative example 11 |
|---|---|---|---|---|---|---|
| Water | To 100 | To 100 | To 100 | To 100 | To 100 | To 100 |
| Disodium EDTA | 0.05 | 0.05 | 0.05 | 0.05 | 0.05 | 0.05 |
| Propanediol | 10 | 10 | 10 | 10 | 10 | 10 |
| Ascorbic acid | 25 | 25 | 25 | 25 | 25 | 25 |
| Acid yellow 23 | 0.0007 | 0.0007 | 0.0007 | 0.0007 | 0.0007 | 0.0007 |
| Glutathione | 0.1 | 0.1 | 0.1 | 0.1 | 0.1 | 0.1 |
| Sodium hyaluronate | 0.4 | 0.4 | 0.4 | 0.4 | 0.4 | 0.4 |
| Xanthan gum | — | — | — | — | — | — |
| Beta-glucan | — | — | — | — | — | — |
| Biosaccharide gum-1 | — | — | — | — | — | — |
| Dimethicone | 2.5 | 2.5 | 2.5 | 2.5 | 2.5 | 2.5 |
| Hydrogenated $C_{6-14}$ olefin polymers | 1.85 | — | — | — | — | — |
| Methyl trimethicone | — | — | — | 1.85 | — | — |
| Diphenylsiloxy phenyl trimethicone | — | — | — | — | 1.85 | — |
| $C_{18-21}$ alkane | — | — | — | — | — | 1.85 |
| Meadowfoam seed oil | — | 1.85 | — | — | — | — |
| Helianthus Annuus (sunflower) seed oil | — | — | 1.85 | — | — | — |
| Sgualane | — | — | — | — | — | — |
| Tocopherol | 0.5 | 0.5 | 0.5 | 0.5 | 0.5 | 0.5 |
| *Solanum lycopersicum* (tomato) fruit lipids | 0.0005 | 0.0005 | 0.0005 | 0.0005 | 0.0005 | 0.0005 |
| Caprylic/capric triglyceride | — | — | — | — | — | — |
| Cetyl 2-ethyl hexanoate | — | — | — | — | — | — |
| Polysorbate 20 | — | — | — | — | — | — |
| PEG-60 hydrogenated castor oil | — | — | — | — | — | — |
| Fragrance | 0.15 | 0.15 | 0.15 | 0.15 | 0.15 | 0.15 |

Figure 4:
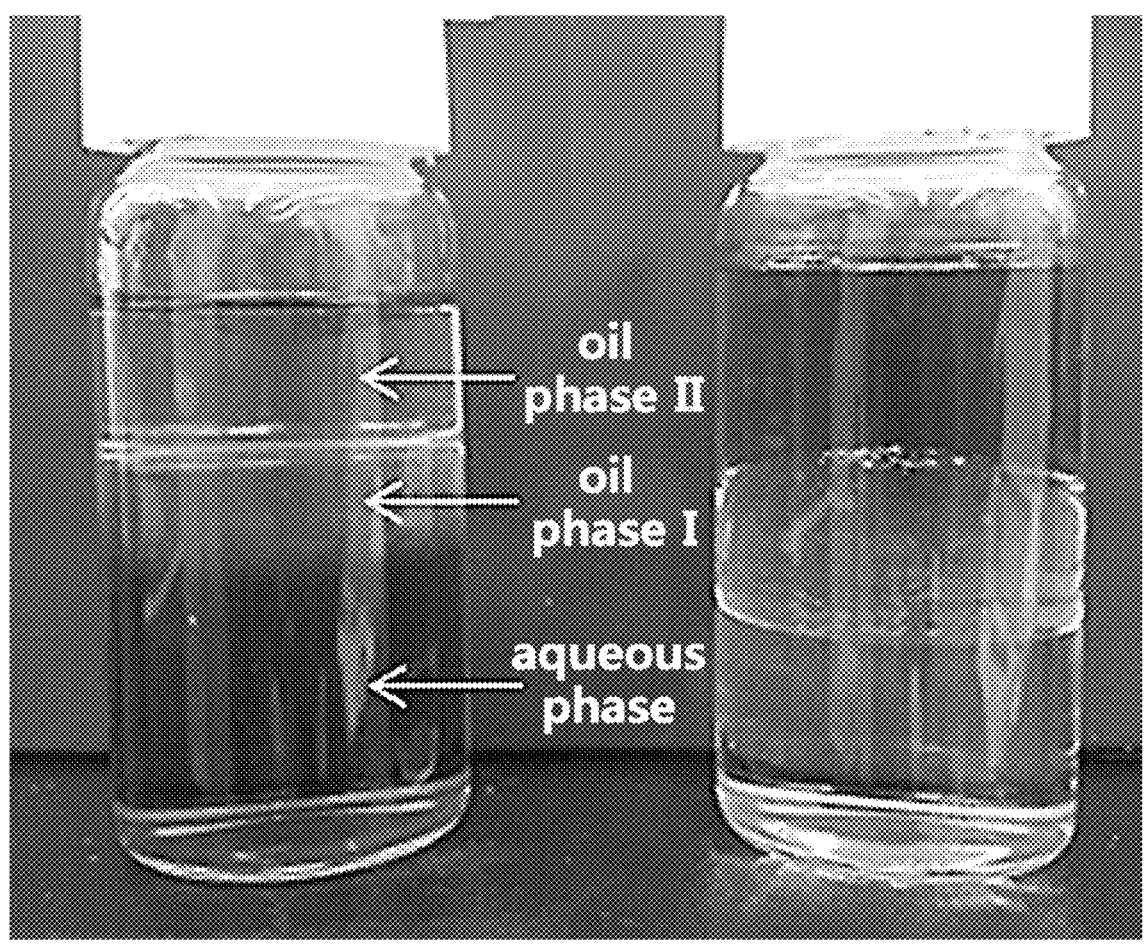
FIG. 4 is the photograph of the composition comprising an oil layer consisting of double layer, according to one test example of the present disclosure.
Figure 5:
FIG. 5 is the photograph showing the test results of the layer separation of the composition comprising an oil layer consisting of double layer, according to one test example of the present disclosure.
Figure 6:
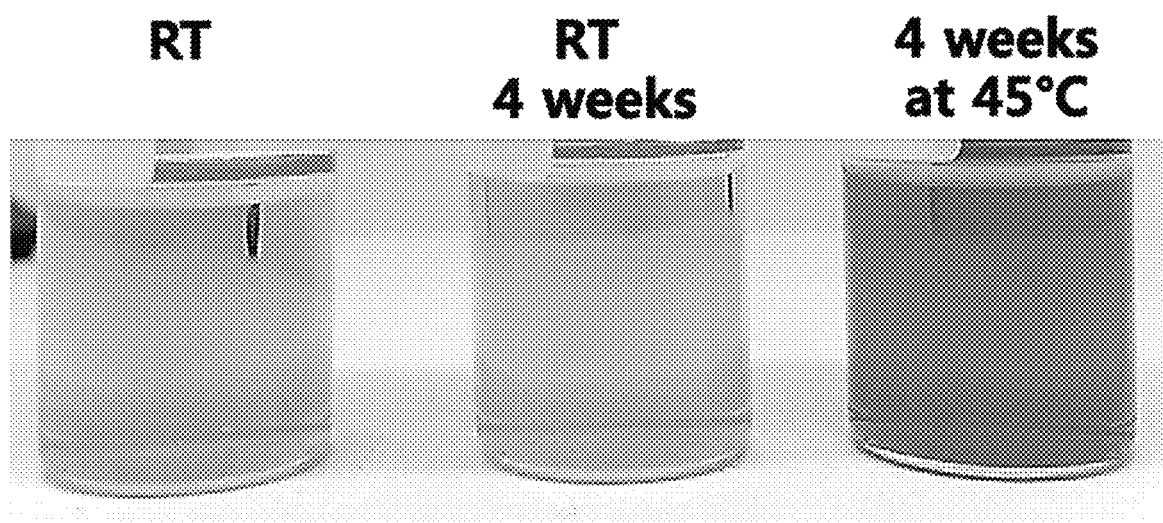
FIG. 6 is the photograph showing the test results of the discoloration of the example, according to one test example of the present disclosure.
Figure 7:
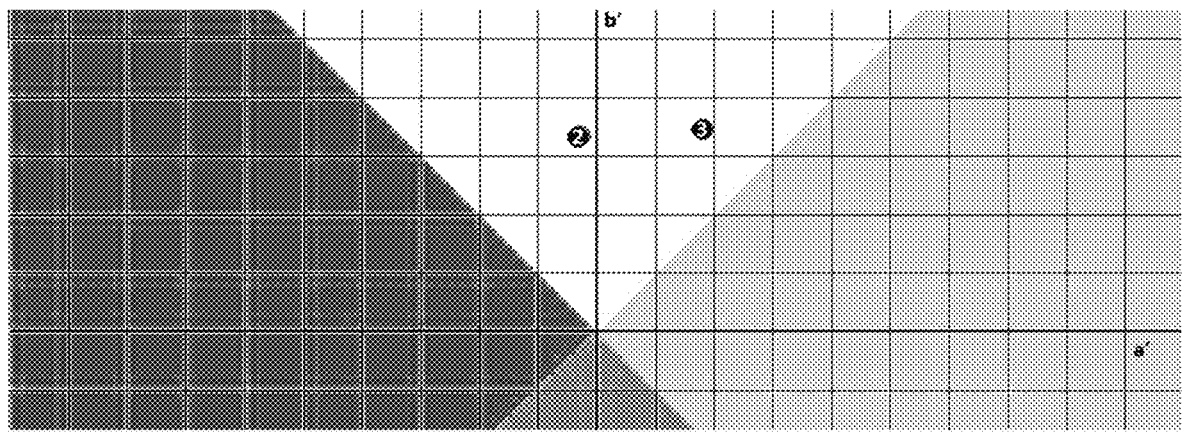
FIG. 7 is the figure showing the chromatic differential graph based on the test results of the discoloration of the example, according to one test example of the present disclosure.
Figure 8:
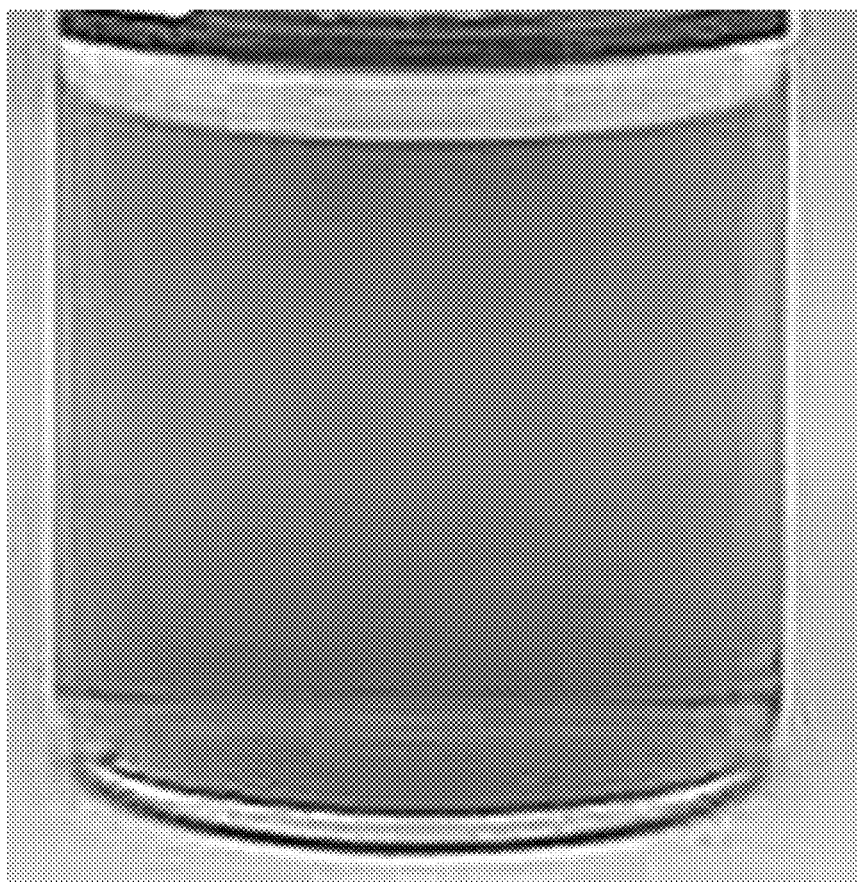
FIG. 8 is the photograph showing the test results of the discoloration of the comparison example, according to one test example of the present disclosure.
Figure 9:
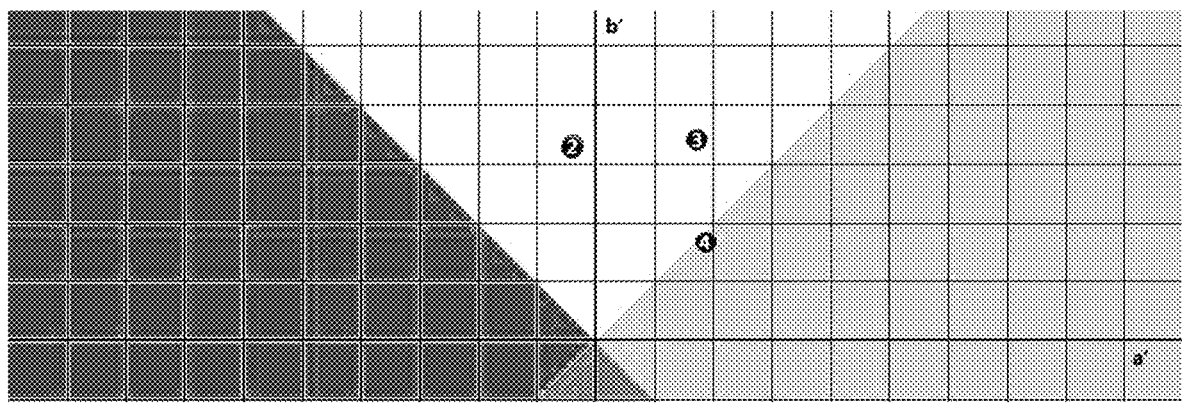
FIG. 9 is the figure showing the chromatic differential graph based on the test results of the discoloration of the comparison example, according to one test example of the present disclosure.

The layer separation was observed after shaking and mixing the cosmetic composition of Table 5. It was confirmed that in Examples 20 to 22, the layer separation occurred into three layers after shaking and mixing, and the layer separation occurred within 4 minutes. However, it was confirmed that in Comparative Examples 9 to 11, after being shaken and mixed, the layers were not recovered to three layers, but the first oil layer and the second oil layer were mixed with each other. FIG. 4 shows Example 22 and FIG. 5 shows Example 21. Thus, it can be confirmed that in the case of using, as the second oil layer, the hydrogenated $C_{6-14}$ olefin polymer, meadowfoam seed oil or sunflower seed used in Examples 20 to 22, the separation into three layers occurred well.

Discoloration Test According to the Presence of the Oil Layer (1) When the Oil Layer is Present Discoloration test was performed with the configurations of Example 22 of Table 5 and Comparative Example 7 of Table 4. Chromatic differential data was obtained and shown in Tables 6 and 7 (see FIGS. 6 to 9). Comparative Example 7 is a value obtained from the tests conducted for 4 weeks at 45° C.

TABLE 6

| | Oil layer present | L | a | b |
|---|---|---|---|---|
| 1 | Room temperature | 28.88 | −3.84 | 33.09 |
| 2 | 4 weeks at room temperature | 29.28 | −4.1 | 32.61 |
| 3 | 4 weeks at 45° C. | 20.09 | 17.22 | 34.07 |

TABLE 7

| | | L | a | b |
|---|---|---|---|---|
| 1 | Comparative example 7 | 10.12 | 18.86 | 16.7 |

In Tables 6 and 7, L denotes a brightness value, a denotes a redness value, and b denotes a yellowness value. The degree of discoloration is judged from both a and b values, and in the case of vitamin C, the yellow color becomes stronger, and as more discoloration progresses, it shows more red color. As shown in Table 6, Example 22, which is one embodiment of the present invention, showed a value close to yellow even when stored for 4 weeks at both of room temperature and 45° C., indicating that almost no discoloration occurred. Even when stored at a high temperature of 45° C., the yellowness was slightly increased, and almost no discoloration occurred. In comparison, Comparative Example 7 is discolored to scarlet with stronger a value, and it can be seen that the discoloration occurred a lot.

(2) When No Oil Layer is Present

Figure 10:
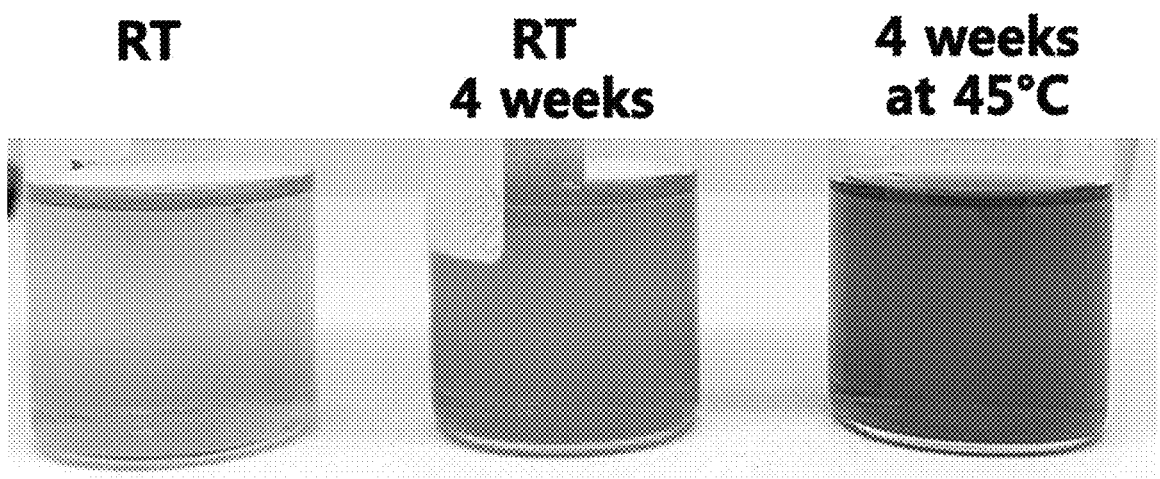
FIG. 10 is the photograph showing the test results of the discoloration of the composition which does not comprise an oil layer, according to one test example of the present disclosure.
Figure 11:
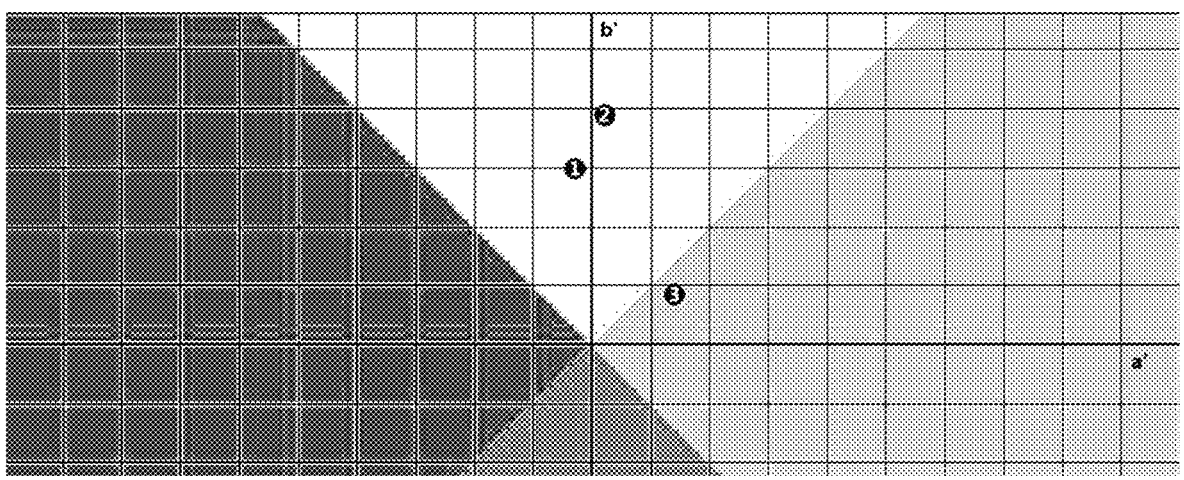
FIG. 11 is the figure showing the chromatic differential graph based on the test results of the discoloration of the composition which does not comprise an oil layer, according to one test example of the present disclosure.

Browning test was performed with the configuration of Comparative Example 12 consisting of only the layer comprising the antioxidant of Example 22. Chromatic differential data were obtained and shown in Table 8 (see FIGS. 10 and 11).

TABLE 8

| | No oil layer | L | a | b |
|---|---|---|---|---|
| 1 | Room temperature | 29.79 | −3.68 | 29.49 |
| 2 | 4 weeks at room temperature | 23.81 | 1.42 | 38.37 |
| 3 | 4 weeks at 45° C. | 4.79 | 13.25 | 7.96 |

When comparing the brightness, redness, and yellowness at the beginning of room temperature storage with and without the oil layer, there is no significant difference. However, when comparing them with 4 weeks after storage at room temperature, it could be seen that when the oil layer is absent, the brightness value is decreased and the redness and yellowness values are greatly increased. In addition, when compared with the case of storage at 45° C., the brightness value is significantly decreased, the redness value is similar, the yellowness value is rather decreased, but this is because the discoloration is deepened and became almost red.

As a result, it was found that the oil layer effectively prevented from the deterioration of antioxidant at room temperature as well as at high temperature than when there is no oil layer.

Vitamin C Oxidation Test Using Iodine Oxidation-Reduction Reaction

Figure 12:
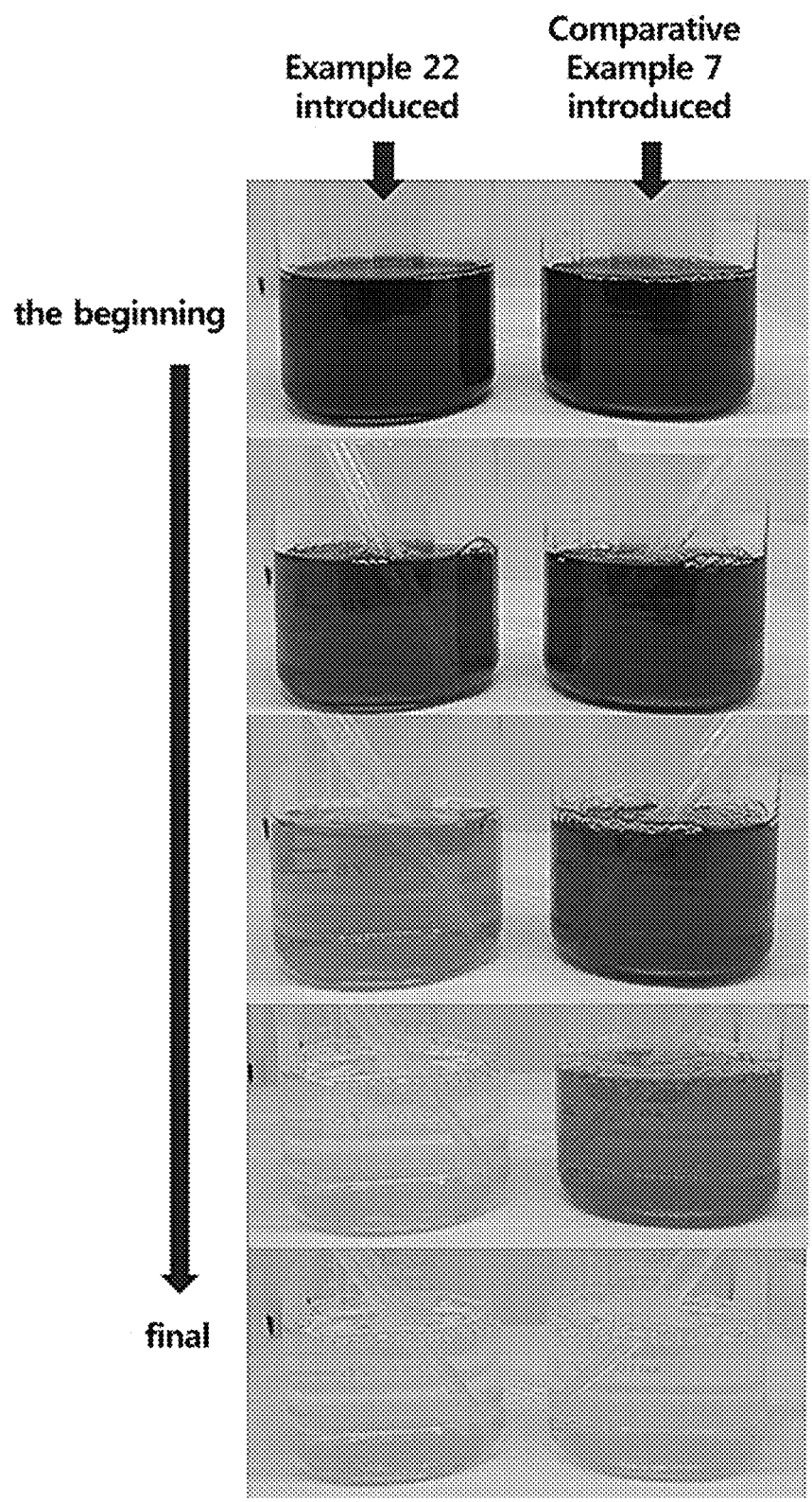
FIG. 12 is the photograph showing the test results of the iodine oxidation-reduction reaction, according to one test example of the present disclosure.

Test using the iodine oxidation-reduction reaction was performed using Example 22 of Table 5 and Comparative Example 7 of Table 4. The oxidation-reduction reaction of iodine as an oxidant and vitamin C as a reducing agent was performed to observe whether brown iodine is reduced and becomes colorless. As a result, it was confirmed that Example 22 becomes brighter in color faster than Comparative Example 7. As a result, it can be seen that Example 22 prevents vitamin C oxidation of the layer containing antioxidant material better than Comparative Example 7 to maintain a high content of vitamin C (see FIG. 12).

Test for Comprising a Fat-Soluble Antioxidant in the Oil Layer

A fat-soluble antioxidant is not dissolved in dimethicone. However, the inventors have found that a fat-soluble antioxidant can be dissolved in squalane oil first, and then can be dissolved by mixing with dimethicone.

Figure 13:
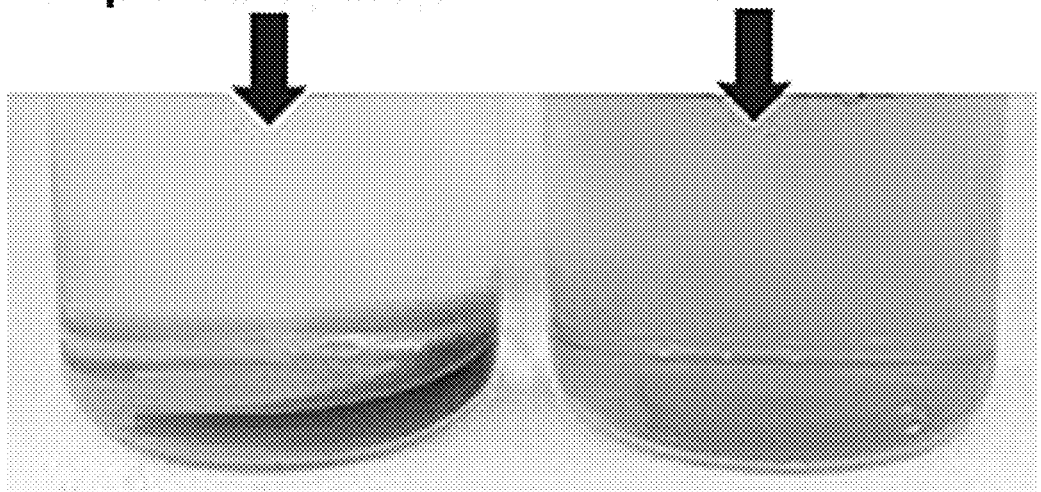
FIG. 13 is the photograph of the composition comprising a fat-soluble antioxidant in the oil layer, according to one test example of the present disclosure.

If tocopherol, which is a fat-soluble component, is mixed with a general silicone-based oil, it is present in a separated state while not being mixed as shown in the left side of FIG. 13. However, it was observed that if tocopherol was dissolved in squalane and then mixed with dimethicone, it was well dissolved as shown in the right image of FIG. 13, so long-term stability was excellent. Accordingly, it can be seen that the oil layer can be formed to be capable of shielding the oxidation of the antioxidant of the layer containing the antioxidant while comprising a fat-soluble antioxidant.

Test for Vitamin C Content to Heat Exposure

External factors that primarily affect the decrease in the titers of vitamins include heat and air exposure. Thus, after exposing the samples of Example 22 of Table 5 and Comparative Examples 7 and 12 of Table 4 to heat, the content ratio of vitamin C after exposure with respect to the total weight of vitamin C was measured. The measurement was analyzed by HPLC and the measurement wavelength was 230 nm. The measurement results are shown in Table 9.

TABLE 9

| | Content of vitamin C (wt. %) |
|---|---|
| Example 22 | 90.73 |
| Comparative Example 12 | 70.83 |
| Comparative Example 7 | 81.42 |

Example 22 is a sample comprising a double layer of dimethicone and a sunflower seed oil; Comparative Example 12 is a sample comprising no oil layer; and Comparative Example 7 is a sample comprising a caprylic/capric triglyceride oil layer.

Example 22 and Comparative Example 12 are the results obtained by measuring the content after storing for 4 weeks at 45° C., and Comparative Example 7 are the result obtained by leaving it for 3 hours at 30° C. From the results, it can be seen that in Example 22, the titer was maintained because there was no change in the content of vitamin C, as compared to Comparative Example 12 in which there is no oil layer and thus is directly exposed to the air layer. In addition, it was confirmed that the composition contains more vitamin C, even though it was exposed at a higher temperature for a longer time as compared to Comparative Example 7 using the oil used in the prior art. As a result, it was confirmed that the cosmetic composition containing vitamin C according to the present disclosure not only had an effect of preventing oxidation against air exposure but also prevented the destruction of vitamin C even at a high temperature.

The present invention may provide the following embodiments as one embodiment.

The first embodiment may provide a cosmetic composition comprising a double layer, comprising a layer comprising an antioxidant, and an oil layer covering the surface of said layer, wherein said oil layer comprises one or more oils selected from the group consisting of dimethicone, methyltrimethicone, hydrogenated $C_{6-14}$ olefin polymers, diphenylsiloxy phenyl trimethicone, $C_{18-21}$ alkane, and natural oils.

The second embodiment may provide the cosmetic composition according to the first embodiment, wherein said antioxidant comprises vitamin C.

The third embodiment may provide the cosmetic composition according to one or more of the first embodiment and the second embodiment, wherein the natural oils comprise one or more selected from the group consisting of Camellia Japonica seed oil, Helianthus Annuus (Sunflower) seed oil, Meadowfoam seed oil, olive oil, grapeseed oil and Limnanthes alba seed oil.

The fourth embodiment may provide the cosmetic composition according to one or more of the first embodiment to the third embodiment, wherein the layer comprising the antioxidant further comprises a thickener.

The fifth embodiment may provide the cosmetic composition according to one or more of the first embodiment to the fourth embodiment, wherein said thickener comprises one or more selected from the group consisting of hyaluronate, xanthan gum, β-glucan and biosaccharide gum-1.

The sixth embodiment may provide the cosmetic composition according to one or more of the first embodiment to the fifth embodiment, wherein said oil layer further comprises squalane and a fat-soluble antioxidant.

The seventh embodiment may provide the cosmetic composition according to one or more of the first embodiment to the sixth embodiment, wherein said fat-soluble antioxidant comprises one or more selected from the group consisting of tocopherol, lycopene and retinol.

The eighth embodiment may provide the cosmetic composition according to one or more of the first embodiment to the seventh embodiment, wherein said oil layer is comprised as a double layer consisting of a first oil layer and a second oil layer, and wherein said first oil layer comprises one or more oils selected from the group consisting of dimethicone, methyltrimethicone, hydrogenated $C_{6-14}$ olefin polymers, diphenylsiloxy phenyl trimethicone, $C_{18-21}$ alkane, and natural oils, and said second oil layer, which covers the surface of said first oil layer, comprises hydrogenated $C_{6-14}$ olefin polymers or vegetable oils.

The ninth embodiment may provide the cosmetic composition according to one or more of the first embodiment to the eighth embodiment, wherein the vegetable oils of said second oil layer comprise one or more selected from the group consisting of Meadowfoam seed oil, Helianthus Annuus (Sunflower) seed oil, Camellia Japonica seed oil, olive oil, grapeseed oil and Limnanthes alba seed oil.

The tenth embodiment may provide the cosmetic composition according to one or more of the first embodiment to the ninth embodiment, further comprising squalane and a fat-soluble antioxidant.

The eleventh embodiment may provide the cosmetic composition according to one or more of the first embodiment to the tenth embodiment, wherein said fat-soluble antioxidant comprises tocopherol, lycopene or a combination thereof.

The twelfth embodiment may provide the cosmetic composition according to one or more of the first embodiment to the eleventh embodiment, wherein the amount of the antioxidant is 15 to 35 wt. % with respect to the total weight of the composition.

The thirteenth embodiment may provide the cosmetic composition according to one or more of the first embodiment to the twelfth embodiment, wherein said oils are comprised in an amount of 3 to 12 wt. % with respect to the total weight of the composition.

The fourteenth embodiment may provide the cosmetic composition according to one or more of the first embodiment to the thirteenth embodiment, wherein the weight ratio of the first oil layer to the second oil layer is 30:1 to 1:30.

The invention claimed is:

1. A cosmetic composition, consisting of a double layer of an antioxidant-containing layer and an oil layer covering a surface of the antioxidant-containing layer,
   wherein the oil layer comprises one or more oils selected from the group consisting of dimethicone and methyltrimethicone,
   wherein the antioxidant-containing layer consists of water and an antioxidant, and optionally a thickener, said antioxidant comprising vitamin C,
   wherein an amount of the antioxidant is 15 to 35 wt. % with respect to a total weight of the composition, and
   wherein the oil layer is in an amount of 3 to 12 wt. % with respect to the total weight of the composition.

2. The cosmetic composition according to claim 1, wherein the antioxidant-containing layer consists of the water, the antioxidant, and the thickener.

3. The cosmetic composition according to claim 2, wherein the thickener is one or more selected from the group consisting of hyaluronate, xanthan gum, β-glucan, and biosaccharide gum-1.

4. The cosmetic composition according to claim 1, wherein the oil layer further comprises squalane and a fat-soluble antioxidant.

5. The cosmetic composition according to claim 4, wherein the fat-soluble antioxidant comprises one or more selected from the group consisting of tocopherol, lycopene, and retinol.

\* \* \* \* \*